US009452039B2

(12) United States Patent
Snow

(10) Patent No.: US 9,452,039 B2
(45) Date of Patent: Sep. 27, 2016

(54) VASCULAR FILTER

(71) Applicant: Merit Medical Systems, Inc., South Jordan, UT (US)

(72) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 563 days.

(21) Appl. No.: 13/774,598

(22) Filed: Feb. 22, 2013

(65) Prior Publication Data

US 2013/0226224 A1  Aug. 29, 2013

Related U.S. Application Data

(60) Provisional application No. 61/602,429, filed on Feb. 23, 2012.

(51) Int. Cl.
*A61M 29/00* (2006.01)
*A61F 2/01* (2006.01)

(52) U.S. Cl.
CPC ............ *A61F 2/01* (2013.01); *A61F 2002/011* (2013.01); *A61F 2002/016* (2013.01); *A61F 2230/005* (2013.01); *A61F 2230/0058* (2013.01); *A61F 2230/0067* (2013.01)

(58) Field of Classification Search
CPC ............... A61F 2/00; A61F 2/01; A61F 2/02
See application file for complete search history.

(56) References Cited

U.S. PATENT DOCUMENTS

| 4,132,650 | A | 1/1979 | Krisch et al. |
| 4,494,531 | A | 1/1985 | Gianturco |
| 4,619,246 | A | 10/1986 | Molgaard-Nielsen |
| 4,781,177 | A | 11/1988 | Lebigot |
| 4,832,055 | A | 5/1989 | Palestrant |
| 4,900,312 | A | 2/1990 | Nadeau |
| 5,133,733 | A | 7/1992 | Rasmussen et al. |
| 5,234,458 | A | 8/1993 | Metais |
| 5,242,462 | A | 9/1993 | El-Nounou et al. |
| 5,312,479 | A | 5/1994 | Weinstein et al. |
| 5,324,304 | A | 6/1994 | Rasmussen |
| 5,370,657 | A | 12/1994 | Irie |
| 5,375,612 | A | 12/1994 | Cottenceau et al. |
| 5,437,655 | A | 8/1995 | Bartholomew |

(Continued)

FOREIGN PATENT DOCUMENTS

| EP | 1987800 | 4/2008 |
| JP | 61/41444 | 5/1994 |

(Continued)

OTHER PUBLICATIONS

Office Action dated Oct. 3, 2013 for U.S. Appl. No. 12/722,484.

(Continued)

*Primary Examiner* — Gregory Anderson
(74) *Attorney, Agent, or Firm* — Stoel Rives LLP

(57) ABSTRACT

A filter, configured to be disposed within a body lumen, such as within the vasculature. The filter may include a plurality of struts, configured to interact with the body lumen wall in order to stabilize the position of the filter and to create a filtering structure. Each strut may have two or more apexes configured to contact the body lumen wall. In some embodiments the filter may be integrally formed form a single tube of material.

33 Claims, 11 Drawing Sheets

(56) References Cited

U.S. PATENT DOCUMENTS

| | | |
|---|---|---|
| 5,484,474 A | 1/1996 | Weinstein et al. |
| 5,601,568 A | 2/1997 | Chevillon et al. |
| 5,626,605 A | 5/1997 | Irie et al. |
| 5,634,942 A | 6/1997 | Chevillon et al. |
| 5,669,933 A | 9/1997 | Simon et al. |
| 5,709,704 A | 1/1998 | Nott et al. |
| 5,795,322 A | 8/1998 | Boudewijn |
| 5,810,874 A | 9/1998 | Lefebvre |
| 5,836,968 A | 11/1998 | Simon et al. |
| 5,836,969 A | 11/1998 | Kim |
| 5,853,420 A | 12/1998 | Chevillon et al. |
| 5,879,381 A | 3/1999 | Moriuchi |
| 5,954,741 A | 9/1999 | Fox |
| 5,976,172 A | 11/1999 | Homsma et al. |
| 5,984,947 A | 11/1999 | Smith |
| 6,007,558 A | 12/1999 | Ravenscroft et al. |
| 6,013,093 A | 1/2000 | Nott et al. |
| 6,059,825 A | 5/2000 | Hobbs |
| 6,099,549 A | 8/2000 | Bosma et al. |
| 6,117,165 A | 9/2000 | Becker |
| 6,156,055 A | 12/2000 | Ravenscroft |
| 6,193,739 B1 | 2/2001 | Chevillon et al. |
| 6,214,025 B1 | 4/2001 | Thistle et al. |
| 6,241,746 B1 | 6/2001 | Bosma et al. |
| 6,258,026 B1 | 7/2001 | Ravenscroft et al. |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,306,141 B1 | 10/2001 | Jervis |
| 6,328,719 B1 | 12/2001 | Holtermann et al. |
| 6,347,711 B1 | 2/2002 | Goebel et al. |
| 6,391,045 B1 | 5/2002 | Kim |
| 6,428,559 B1 | 8/2002 | Johnson |
| 6,436,121 B1 | 8/2002 | Blom |
| 6,443,972 B1 | 9/2002 | Bosma |
| 6,461,370 B1 | 10/2002 | Gray et al. |
| 6,468,290 B1 | 10/2002 | Weldon et al. |
| 6,485,501 B1 | 11/2002 | Green |
| 6,506,205 B2 | 1/2003 | Goldberg et al. |
| 6,511,496 B1 | 1/2003 | Huter et al. |
| 6,527,962 B1 | 3/2003 | Nadal |
| 6,540,722 B1 | 4/2003 | Boyle et al. |
| 6,540,768 B1 | 4/2003 | Diaz et al. |
| 6,589,266 B2 | 7/2003 | Whitcher et al. |
| 6,596,011 B2 | 7/2003 | Johnson et al. |
| 6,620,183 B2 | 9/2003 | DiMatteo |
| 6,623,506 B2 | 9/2003 | McGuckin, Jr. et al. |
| 6,656,203 B2 | 12/2003 | Roth et al. |
| 6,660,021 B1 | 12/2003 | Palmer et al. |
| 6,726,701 B2 | 4/2004 | Gilson et al. |
| 6,783,538 B2 | 8/2004 | McGuckin, Jr. et al. |
| 6,793,665 B2 | 9/2004 | McGuckin, Jr. et al. |
| 6,932,831 B2 | 8/2005 | Forber |
| 6,939,361 B1 | 9/2005 | Kleshinski |
| 6,958,074 B2 | 10/2005 | Russell |
| 6,989,021 B2 | 1/2006 | Bosma |
| 6,991,641 B2 | 1/2006 | Diaz et al. |
| 7,147,649 B2 | 12/2006 | Thomas |
| 7,179,275 B2 | 2/2007 | McGuckin |
| 7,261,731 B2 | 8/2007 | Patel |
| 7,279,000 B2 | 10/2007 | Cartier et al. |
| 7,314,477 B1 | 1/2008 | Ravenscroft et al. |
| 7,323,002 B2 | 1/2008 | Johnson et al. |
| 7,329,227 B2 | 2/2008 | Schramm |
| 7,329,269 B2 | 2/2008 | Shapiro et al. |
| 7,329,277 B2 | 2/2008 | Addonizio et al. |
| 7,338,512 B2 | 3/2008 | McGuckin, Jr. et al. |
| 7,344,549 B2 | 3/2008 | Boyle et al. |
| 7,399,308 B2 | 7/2008 | Borillo et al. |
| 7,534,251 B2 | 5/2009 | WasDyke |
| 7,544,202 B2 | 6/2009 | Cartier et al. |
| 7,582,100 B2 | 9/2009 | Johnson |
| 7,625,390 B2 | 12/2009 | Hendriksen et al. |
| 7,699,865 B2 | 4/2010 | Johnson et al. |
| 7,699,867 B2 | 4/2010 | Hendriksen et al. |
| 7,704,266 B2 | 4/2010 | Thinnes, Jr. et al. |
| 7,704,267 B2 | 4/2010 | Tessmer |
| 7,736,383 B2 | 6/2010 | Bressler et al. |
| 7,749,246 B2 | 7/2010 | McGuckin et al. |
| 7,763,045 B2 | 7/2010 | Osborne |
| 7,771,452 B2 | 8/2010 | Pal et al. |
| 7,780,694 B2 | 8/2010 | Palmer et al. |
| 7,794,473 B2 | 9/2010 | Tessmer et al. |
| 7,803,171 B1 | 9/2010 | Uflacker |
| 7,862,577 B2 | 1/2011 | Gray et al. |
| 7,887,561 B2 | 2/2011 | McGuckin, Jr. et al. |
| 7,909,847 B2 | 3/2011 | McGuckin, Jr. et al. |
| 7,931,664 B2 | 4/2011 | Gray et al. |
| 7,959,647 B2 | 6/2011 | Palmer |
| 7,967,838 B2 | 6/2011 | Chanduszko et al. |
| 7,972,353 B2 | 7/2011 | Hendriksen et al. |
| 7,976,562 B2 | 7/2011 | Bressler et al. |
| 7,996,993 B2 | 8/2011 | Gray et al. |
| 8,025,675 B2 | 9/2011 | Shirley et al. |
| 8,029,529 B1 | 10/2011 | Chanduszko |
| 8,043,322 B2 | 10/2011 | Hendriksen et al. |
| 8,057,506 B2 | 11/2011 | Gilson et al. |
| 8,057,507 B2 | 11/2011 | Horan et al. |
| 8,062,326 B2 | 11/2011 | McGuckin, Jr. et al. |
| 8,062,327 B2 | 11/2011 | Chanduszko et al. |
| 8,062,328 B2 | 11/2011 | Hallisey |
| 8,092,484 B2 | 1/2012 | Kashkarov et al. |
| 8,092,485 B2 | 1/2012 | Lapid |
| 8,100,936 B2 | 1/2012 | McGuckin, Jr. et al. |
| 8,105,349 B2 | 1/2012 | Hendriksen et al. |
| 8,118,828 B2 | 2/2012 | Cartier et al. |
| 8,133,251 B2 | 3/2012 | Ravenscroft et al. |
| 8,133,252 B2 | 3/2012 | Davis et al. |
| 8,162,972 B2 | 4/2012 | McGuckin, Jr. et al. |
| 8,167,901 B2 | 5/2012 | Hendriksen et al. |
| 8,211,140 B2 | 7/2012 | McGunkin, Jr. et al. |
| 8,246,648 B2 | 8/2012 | Tekulve |
| 8,246,650 B2 | 8/2012 | Osborne |
| 8,246,651 B2 | 8/2012 | Hendriksen et al. |
| 8,252,017 B2 | 8/2012 | Paul, Jr. et al. |
| 8,252,019 B2 | 8/2012 | Fleming, III |
| 8,267,954 B2 | 9/2012 | Decant, Jr. et al. |
| 8,282,668 B2 | 10/2012 | McGuckin, Jr. et al. |
| 8,317,818 B2 | 11/2012 | Kashkarov et al. |
| 8,333,785 B2 | 12/2012 | Chanduszko et al. |
| 8,353,926 B2 | 1/2013 | Silver |
| 8,366,736 B2 | 2/2013 | Thinnes, Jr. et al. |
| 8,383,926 B2 | 2/2013 | Plissonnier et al. |
| 8,430,903 B2 | 4/2013 | Chanduszko et al. |
| 8,475,488 B2 | 7/2013 | Cartier et al. |
| 8,734,480 B2 | 5/2014 | Snow |
| 9,028,525 B2 | 5/2015 | Hallisey |
| 2001/0000799 A1 | 5/2001 | Wessman et al. |
| 2001/0039432 A1 | 11/2001 | Whitcher et al. |
| 2002/0058911 A1 | 5/2002 | Gilson et al. |
| 2002/0062134 A1 | 5/2002 | Barbut et al. |
| 2002/0111647 A1 | 8/2002 | Khairkhahan et al. |
| 2003/0109897 A1 | 6/2003 | Walak et al. |
| 2003/0181942 A1 | 9/2003 | Sutton et al. |
| 2004/0082966 A1 | 4/2004 | Wasdyke |
| 2004/0087999 A1 | 5/2004 | Bosma et al. |
| 2004/0116959 A1 | 6/2004 | McGuckin |
| 2004/0220610 A1 | 11/2004 | Kreidler et al. |
| 2005/0004596 A1 | 1/2005 | McGuckin, Jr. et al. |
| 2005/0015111 A1 | 1/2005 | McGuckin et al. |
| 2005/0080447 A1 | 4/2005 | McGuckin, Jr. et al. |
| 2005/0222604 A1 | 10/2005 | Schaeffer |
| 2005/0267515 A1 | 12/2005 | Oliva et al. |
| 2005/0288704 A1 | 12/2005 | Cartier et al. |
| 2005/0288705 A1 | 12/2005 | Gilson |
| 2006/0009799 A1 | 1/2006 | Kleshinski et al. |
| 2006/0041271 A1 | 2/2006 | Bosma et al. |
| 2006/0079928 A1 | 4/2006 | Cartier |
| 2006/0079930 A1 | 4/2006 | McGuckin et al. |
| 2006/0100659 A1 | 5/2006 | Dinh et al. |
| 2006/0106417 A1 | 5/2006 | Tessmer |
| 2006/0206138 A1 | 9/2006 | Eidenschink |
| 2007/0005095 A1 | 1/2007 | Osborne |
| 2007/0141107 A1 | 6/2007 | Kutryk |

(56) References Cited

U.S. PATENT DOCUMENTS

| | | |
|---|---|---|
| 2007/0162048 A1 | 7/2007 | Quinn et al. |
| 2007/0162071 A1 | 7/2007 | Burkett et al. |
| 2007/0167974 A1 | 7/2007 | Cully et al. |
| 2007/0173885 A1 | 7/2007 | Cartier |
| 2007/0191932 A1 | 8/2007 | Kutryk |
| 2007/0198050 A1 | 8/2007 | Ravenscroft |
| 2008/0027481 A1 | 1/2008 | Gilson |
| 2008/0033479 A1 | 2/2008 | Silver |
| 2008/0097518 A1 | 4/2008 | Thinnes |
| 2008/0234722 A1 | 9/2008 | Bonnette et al. |
| 2008/0275487 A1 | 11/2008 | Fleming |
| 2008/0275492 A1 | 11/2008 | Farmiga |
| 2009/0043332 A1 | 2/2009 | Sullivan et al. |
| 2009/0069840 A1 | 3/2009 | Hallisey |
| 2009/0198270 A1 | 8/2009 | McGuckin, Jr. et al. |
| 2009/0254117 A1 | 10/2009 | Pakter |
| 2009/0299403 A1 | 12/2009 | Chanduszko et al. |
| 2009/0299404 A1 | 12/2009 | Chanduszko et al. |
| 2009/0306703 A1 | 12/2009 | Kashkarov et al. |
| 2010/0049238 A1 | 2/2010 | Simpson |
| 2010/0174310 A1 | 7/2010 | Tessmer |
| 2010/0185229 A1 | 7/2010 | Horan et al. |
| 2010/0185230 A1 | 7/2010 | Horan et al. |
| 2010/0198252 A1 | 8/2010 | Beyer et al. |
| 2010/0318115 A1 | 12/2010 | Chanduszko et al. |
| 2011/0040321 A1 | 2/2011 | Cartier |
| 2011/0082538 A1 | 4/2011 | Dahlgren et al. |
| 2011/0106133 A1 | 5/2011 | O'Connell et al. |
| 2011/0137335 A1 | 6/2011 | Hallisey et al. |
| 2011/0166593 A1 | 7/2011 | Paul, Jr. |
| 2011/0202086 A1 | 8/2011 | Bates |
| 2011/0208233 A1 | 8/2011 | McGuckin, Jr. et al. |
| 2012/0016471 A1 | 1/2012 | Salahieh et al. |
| 2012/0089173 A1 | 4/2012 | Tekulve |
| 2012/0109181 A1 | 5/2012 | Hallisey |
| 2012/0130418 A1 | 5/2012 | Jenson et al. |
| 2012/0184985 A1 | 7/2012 | Ravenscroft et al. |
| 2012/0245622 A1 | 9/2012 | McGuckin, Jr. et al. |
| 2013/0018387 A1 | 1/2013 | Diamant |
| 2013/0035713 A1 | 2/2013 | Snow |
| 2013/0035714 A1 | 2/2013 | Snow |
| 2014/0214046 A1 | 7/2014 | Puckett |
| 2015/0045828 A1 | 2/2015 | McArthur et al. |

FOREIGN PATENT DOCUMENTS

| | | |
|---|---|---|
| JP | 2008/154276 | 7/2008 |
| WO | WO01/10342 | 2/2001 |
| WO | WO02/071977 | 9/2002 |
| WO | WO2007/084431 | 7/2007 |
| WO | 2008051294 A2 | 5/2008 |
| WO | WO2008/127328 | 10/2008 |
| WO | WO2009/032834 | 3/2009 |
| WO | WO2010091118 | 8/2010 |

OTHER PUBLICATIONS

Office Action dated Oct. 17, 2013 for U.S. Appl. No. 13/204,492.
Notice of Allowance dated Feb. 14, 2014 for U.S. Appl. No. 13/204,492.
Notice of Allowance dated Feb. 12, 2014 for U.S. Appl. No. 13/204,462.
Boothroyd et al., 'Product Design for Manufacture and Assembly.' 1994, p. 64.
International Preliminary Report for Application No. PCT/US08/75102 dated Sep. 3, 2008.
International Publication and Written Opinion for Application No. PCT/US08/75102 dated Mar. 12, 2009.
Cipolla et al., 'Complications of Vena Cava Filters: A Comprehensive Clinical Review.' OPUS 12 Scientist 2008; vol. 2, No. 2: 11-24.
Katsamouris et al. 'Inferior Vena Cava Filters: In Vitro Comparison of Clot Trapping and Flow Dynamics.' Radiology 1988; 166:361-366.
Prince et al., 'The diameter of the inferior Vena Cava and It's Implications for the Use of Vena Caval Filters.' Radiology 1983; 149:687-689.
Simon et al., 'Comparative Evaluation of Clinically Available Inferior Vena Cava Filters with an In Vitro Physiologic Simulation of the Vena Cava.' Radiology 1993; 189:769-774.
Lorch et al., 'In Vitro Studies of Temporary Vena Cava Filters.' CardioVascular and Interventional Radiology 1998; 21:146-150.
Neuerburg et al., 'New Retrievable Percutaneous Vena Cava Filter: Experimental In Vitro and In Vivo Evaluation.' CardioVascular and Interventional Radiology 1993: 16:224-229.
Reekers et al., 'Evaluation of the Retrievability of the OptEase IVC Filter in an Animal Model.' J Vasc Interv Radiol 2004; 15:261-267.
Kinney, 'Update on Inferior Vena Cava Filters.' J Vasc Intery Radiol 2003; 14:425-440.
Bruckheimer et al., 'In Vitro Evaluation of a Retrievable Low-Profile Nitinol Vena Cava Filter.' J Vasc Interv Radiol 2003; 14:469-474.
Brountzos et al., 'A New Optional Vena Cava Filter: Retrieval at 12 Weeks in an Animal Model.' J Vasc Interv Radiol 2003; 14:763-772.
Ray et al., 'Outcomes with Retrievable Inferior Vena Cava Filters: A Multicenter Study.' J Vasc Interv Radiol 2006; 17:1595-1604.
Kaufman et al., 'Guidelines for the Use of Retrievable and Convertible Vena Cava Filters: Report from the Society of Interventional Radiology Mulitdisciplinary consensus conference.' J Vasc Interv Radiol 2006; 17:449-459.
Kolbeck et al., 'Optional Inferior Vena Cava Filter Retrieval with Retained Thrombus: An In Vitro Model.' J Vasc Intery Radiol 2006; 17:685-691.
Lorch et al., 'Current Practice of Temporary Vena Cava Filter Insertion: A Multicenter Registry.' JVIR 2000; 11:83-88.
Rousseau et al., 'The 6-F Nitinol TrapEase Inferior Vena Cava Filter: Results of a Prospective Multicenter Trial.' J Vasc Interv Radiol 2001; 12:299-304.
Stoneham et al., 'Temporary Inferior Vena Cava Filters: In Vitro Comparison with Permanent IVC Filters.' JVIR 1995; 6:731-736.
Crochet et al., 'Evaluation of the LGM Vena Cava-Tech Infrarenal Vena Cava Filter in and Ovine Venous Thromboembolism Model.' J Vasc Interv Radiol 2001; 12:739-745.
Kaufman, 'Guidelines for the Use of Optional Retrievable Vena Cava Filters.' European Respiratory Disease 2007; 31-34.
Epstein et al., 'Experience with the Amplatz Retrievable Vena Cava Filter.' Radiology 1989; 172:105-110.
Inferior Vena Cava Filter, ISI Interventional & Surgical Innovations LLC. Product Brochure, Copyright 2008.
The Clot Stopper (online). Retrieved from the internet URL:http://www.americanheritage.com/people/articles/web/20060715 -pulmonary-embolism-blood-clot-lazar-greenfield- garman-kimmel-surgery-medical-doctor-surgeon.shtml Summer 2006, vol. 22 Issue 1.
Simon Nitinol Filter, Versatile and Dependable Performance. Bard Peripheral Vascular (online). Retrieved from the internet URL:http://www.bardpv.com_vascular/product.php?p=23 Copyright 2004.
Aegisy Vena Cava Filter. Shenzhen Lifetech Scientific Inc. (online). Retrieved from the internet URL:http://www.lifetechmed.com/english/product/product6.htm Copyright 2005.
Safe Flo Vena Cava Filter (online) Retrieved from the internet <URL:www.rafaelmedical.com>.
Aegisy Vena Cava Filter Product Description (online). Retrieved from the internet URL:http://www.lifetechclinic.com/upload/article/vena/instruction _for_use.htm Accessed Jun. 6, 2008.
Design History (online). Retrieved from the internet URL:http://www.lifetechclinic.com/upload/article/vena/vena_cava_filter.htm Accessed Jun. 6, 2008.
Crux Biomedical, Inc. Inferior Vena Cava Filter System Instructions for Use, IFU P/N 0001 Rev.B, DCO# 0027, Effective Date Feb. 2, 2007.
Smouse, 'Next Generation Filters: Are There Improvements Over the Existing Filters?', Powerpoint Presentation. University of Illinois College of Medicine at Peoria.
Kaufman, 'Vena Cava Filters as a Risk Factor for VTE'. Powerpoint Presentation at the SIR Foundation Jun. 2007 IVC Filter Research Consensus Panel.

(56) References Cited

OTHER PUBLICATIONS

Rectenwald, 'Are All IVC's the Same.' Powerpoint Presentation at the SIR Foundation Jun. 2007 IVC Filter Research Consensus Panel.
Rogers, 'Vena Cava Filter Outcomes.' Powerpoint Presentation at the SIR Foundation Jun. 2007 IVC Filter Research Consensus Panel.
SIR Foundation Research Consensus Panel for the Development of a Research Agenda in Inferior Vena Cava Filters, Jun. 12, 2007—Herndon, VA. Powerpoint Presentation at the SIR Foundation Jun. 2007 IVC Filter Research Consensus Panel.
TrapEase Vena Cava Filter User's Instruction. Cordis Corp.
Corriere et al., 'Vena Cava Filters: An Update.' Future Cardiol 2006: 2(6): 695-707.
Mohan, C. et al. 'Comparative Efficacy and Complications of Vena Caval Filters.' J Vasc Surg 1995; 21:235-246.
Linsenmaier, U. et al., 'Indications, Management, and Complications of Temporary Inferior Vena Cava Filters.' Cardiovascular Intervent, Radiol 1998; 21(6): 464-469.
Asch et al. Radiology 2002; 29:173-176.
Cunliffe et al., 'A Fatal Complication of a Vena Cava Filter Associated with Pulmonary Thromboembolism.' Am J Forensic Med Pathol 2008; 29:173-176.
Joels et al., 'Complications of Inferior Vena Cava Filters.' Am Surg 2003; 69:654-659.
Pulmonary Embolism (online). Retrieved from internet URL:http//www.mayoclinic.com/health/pulmonary-embolism/DS00429/DSECTION=complications by Mayo Clinic Staff Sep. 28, 2007.
Cordis TrapEase Permanent Vena Cava Filter with the VisEase Angiographic Vessel Dilator (on line). Retrieved from <URL:http//www.mitek.com/home.jhtml?loc=USENG&page=viewcontent&contentid=09008b9880ffdcbf&nodekey=1Prod_Info/Type/Endovascular_Disease_Management/Vena_Cava_Filters&parentid=fc0de00100001215> 2000-2008.
Decousus et al., 'A Clinical Trial of Vena Caval Filters in the Prevention of Pulmonary Embolism in Patients with Proximal Deep-Vein Thrombosis.' The New England Journal of Medicine, Feb. 12, 1998; vol. 338, No. 7.
Notice of Allowance for U.S. Appl. No. 12/203,515 dated Jul. 13, 2011.
Restriction Requirement dated Nov. 21, 2011 for U.S. Appl. No. 12/722,484.
Office Action dated Mar. 6, 2012 for U.S. Appl. No. 12/722,484.
Office Action dated Sep. 26, 2012 for U.S. Appl. No. 12/722,484.
International Search Report and Written Opinion dated Jan. 30, 2013 for PCT/US2012/047004.
International Search Report and Written Opinion dated Jan. 30, 2013 for PCT/US2012/047023.
Office Action dated Mar. 29, 2013 for U.S. Appl. No. 13/204,462.
Office Action dated Mar. 29, 2013 for U.S. Appl. No. 13/204,492.
Notice of Allowance dated Mar. 27, 2015 for U.S. Appl. No. 13/286,653.
International Search and Written Opinion dated Jun. 13, 2013 for PCT/US2013/027427.
Office Action dated Apr. 10, 2014 for U.S. Appl. No. 13/286,653.
Notice of Allowance dated Apr. 16, 2014 for U.S. Appl. No. 12/722,484.
Office Action dated Sep. 22, 2014 for U.S. Appl. No. 13/286,653.
International Search Report and Written Opinion dated Nov. 13, 2014 for PCT/US2014/050176.
Extended European Search Report dated Nov. 20, 2014 for EP12821778.3.
Extended European Search Report dated Nov. 20, 2014 for EP12822068.8.
Extended European Search Report dated May 4, 2015 for EP13751892.4.
International Preliminary Report dated Mar. 9, 2010 for PCT/US2008/75102.
International Search Report and Written Opinion dated Feb. 18, 2016 for PCT/US2014/050176.
International Search Report and Written Opinion dated Nov. 10, 2008 for PCT/US2008/75102.
Katsamouris et al., 'Inferior Vena Cava Filters: In Vitro Comparison of Clot Trapping and Flow Dynamics', Radiology 1988, 166:361-366.
Office Action dated Jun. 30, 2016 for U.S. Appl. No. 14/454,297.
"Definition of Coupling: Merriam-Webster: http//www.merriam-webster.com/dictionary/coupling", 2016.

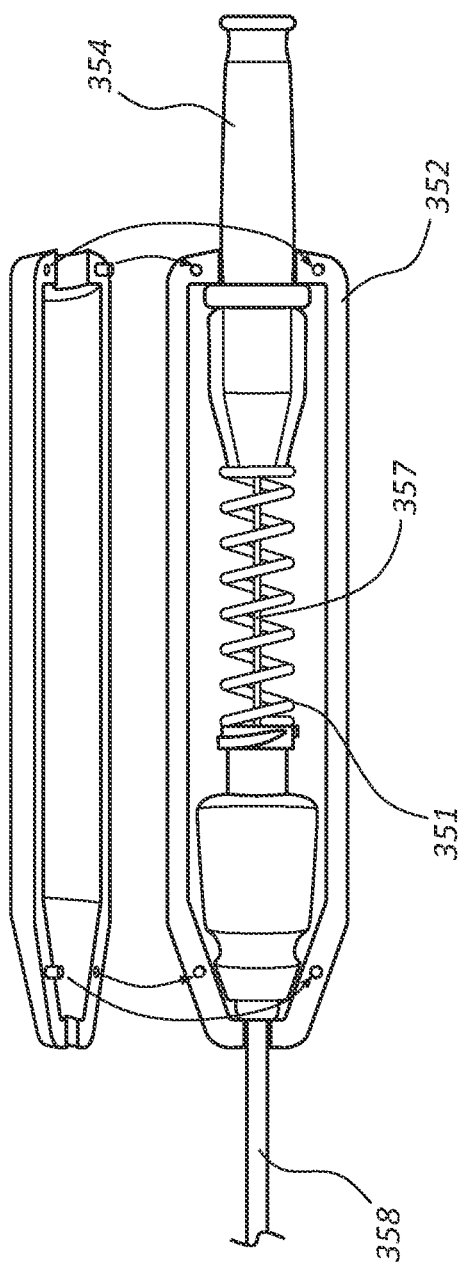
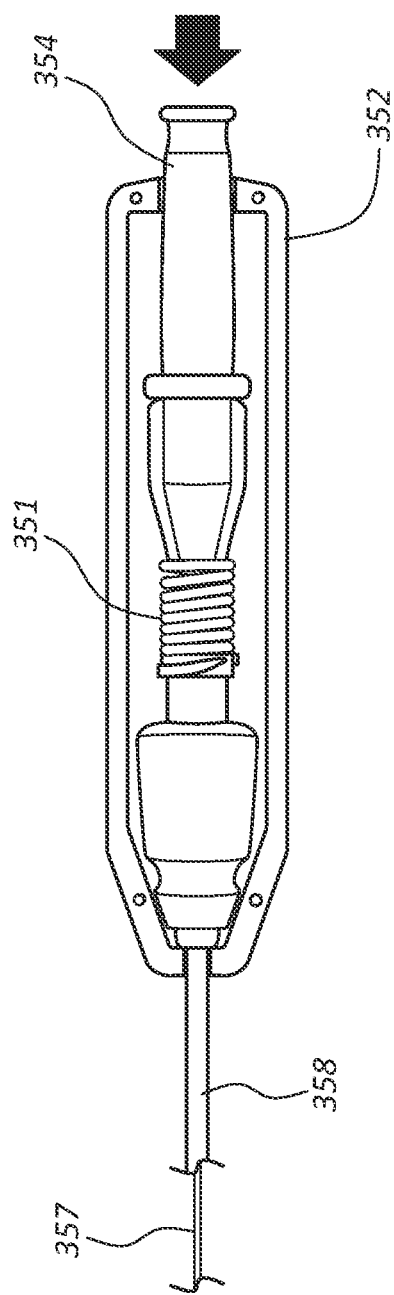
FIG. 8A
FIG. 8B

VASCULAR FILTER

RELATED APPLICATIONS

This application claims priority to U.S. Provisional Application No. 61/602,429 filed on Feb. 23, 2012, titled "Vascular Filter," which is hereby incorporated by reference in its entirety.

TECHNICAL FIELD

The present disclosure relates generally to filters configured to be disposed within a body lumen. More particularly, the present disclosure relates to filters or similar devices that may be configured to capture blood clots within the vasculature, such as within the inferior vena cava.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 8A is a side view of the handle of the delivery system of FIGS. 7A-7C, in a first configuration.

FIG. 8B is a side view of the handle of FIG. 8A in a second configuration.

DETAILED DESCRIPTION

A filter may be configured to be disposed within the vasculature to capture or trap material within a body lumen. For example, a filter may be configured to trap blood clots in the vasculature. In some embodiments, a filter may be disposed within the inferior vena cava and be configured to inhibit pulmonary embolism. Furthermore, a filter may be configured to be removable.

Though many of the examples provided herein may refer to a filter disposed within the inferior vena cava, the present disclosure is applicable to a variety of filters configured to be disposed elsewhere within the vasculature or within other body lumens.

It will be readily understood that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. In the filter embodiments shown herein, the proximal end is defined as the end of the filter configured to be disposed nearest the heart when the filter is disposed within the human body, while the distal end is the opposite end of the filter. Because some filters described below may be deployed from numerous entry points on the body, the terms proximal and distal, with regard to the filter, are not related to the end of the device closest to the practitioner during deployment. With respect to deployment devices disclosed herein, however, the proximal end refers to the end nearest a practitioner when the device is in use.

Figure 1A:
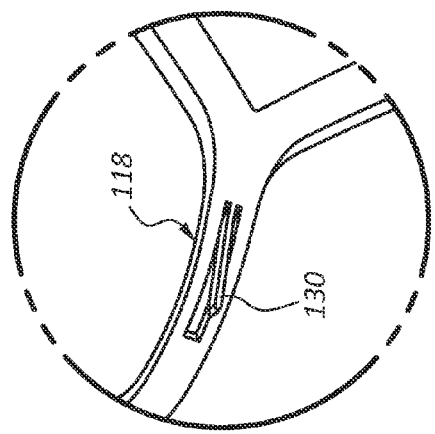
FIG. 1A is a detail view, taken through line 1A-1A, of a portion of the filter of FIG. 1.
Figure 1B:
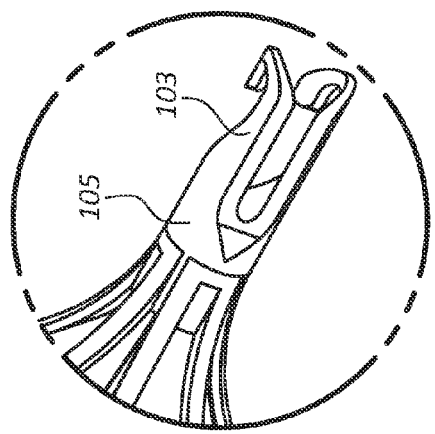
FIG. 1B is a detail view, taken through line 1 B-1 B, of a portion of the filter of FIG. 1.
Figure 1:
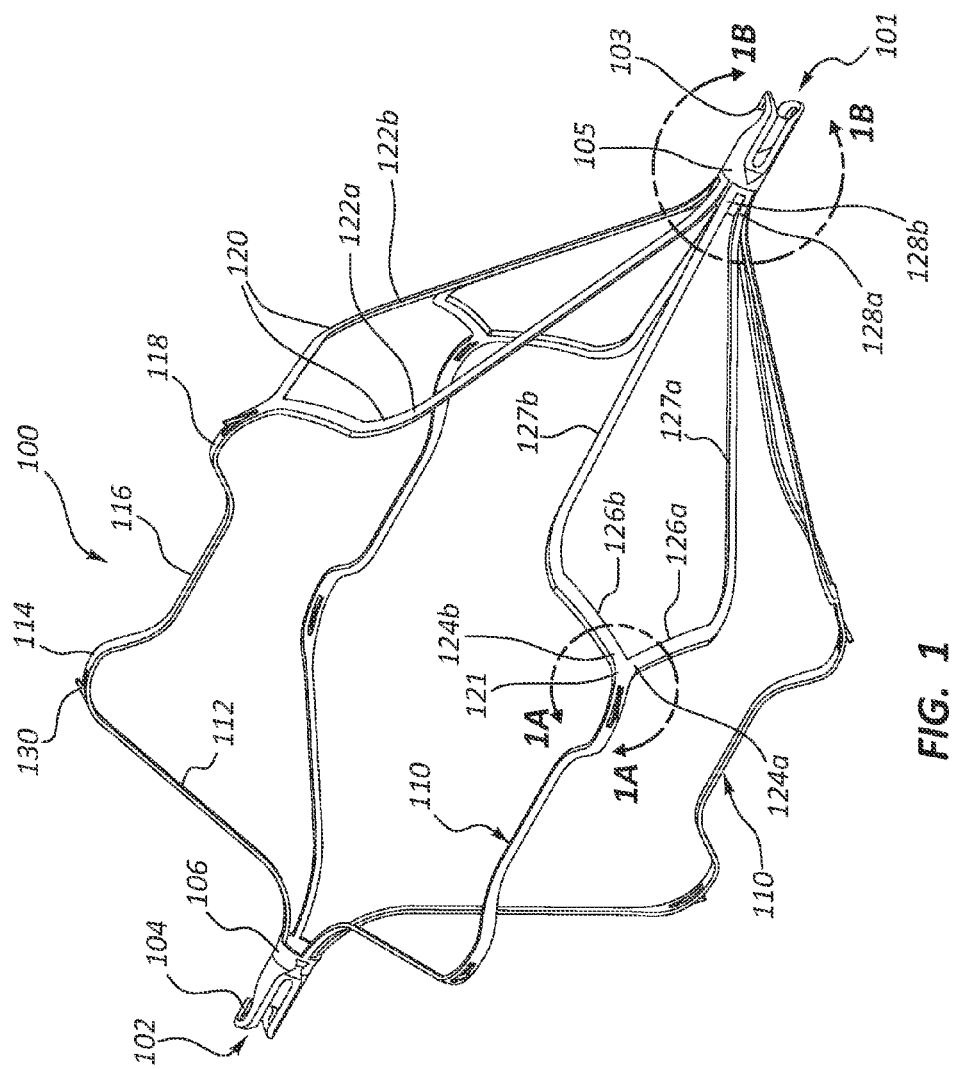
FIG. 1 is a perspective view of a filter.

FIG. 1 is a perspective view of a filter 100 having a proximal end 101 and a distal end 102. The filter 100 of FIG. 1 comprises a proximal axial portion 105 and a distal axial portion 106. Further, the filter 100 may define a longitudinal axis extending from the proximal end 101 to the distal end 102 of the filter 100. The longitudinal axis of the filter, as used herein, refers to an imaginary line running along the longitudinal centerline of the filter. In the embodiment of FIG. 1, for example, the proximal axial portion 105 and the distal axial portion 106 are generally tubular in nature. The longitudinal axis of the filter 100 is substantially collinear with the central axis of an imaginary tubular surface extending between the proximal axial portion 105 and the distal axial portion 106. Some embodiments may not include substantially tubular axial portions such as portions 105, 106 or have a readily identifiable imaginary tubular surface along the center of the filter. In such embodiments, the center axis of the filter may still be understood as a line through the center of the filter. In some embodiments, the filter may be configured such that the center axis of the filter is designed to be disposed substantially along the center axis of a lumen in which the filter is deployed. Thus, in the following description, components of the filter 100 may therefore be described with reference to the longitudinal axis of the filter. (That is, a component may be described as extending radially outward from the longitudinal axis of the filter.)

In the embodiment of FIG. 1, a proximal hook 103 is coupled to the proximal axial portion 105 and distal hook 104 is coupled to the distal axial portion 106. In some embodiments, the hooks 103, 104 may be integrally formed with the proximal 105 and distal 106 axial portions. In some embodiments, one or both of the proximal hook 103 and the distal hook 104 may be used in deploying, retrieving, or repositioning the filter 100. In other embodiments, a filter may include only one hook at either the proximal 101 or distal 102 end of the filter 100.

Filter 100 also includes a plurality of struts 110, which, in the embodiment of FIG. 1, includes four struts 110. In other embodiments the plurality of struts 110 may have more or fewer struts, for example, from three to twelve struts, from five to ten struts, or from six to nine struts, or specifically three, five, six, seven, eight, nine, ten, eleven, or twelve struts. Likewise, while in the embodiment of FIG. 1 each strut 110 of the plurality of struts has substantially the same shape as the other struts 110, in other embodiments different struts on the same filter may have different shapes. Further, though in the embodiment of FIG. 1 the struts 110 are substantially evenly spaced circumferentially around the center axis of the filter 100, in other embodiments the struts 110 may be irregularly spaced.

In the illustrated embodiment, struts 110 are substantially identical in size and shape. Thus, disclosure provided in connection with one strut 110 is equally applicable to the other struts. Furthermore, reference numerals shown in the Figures in connection with one strut 110 may be used to refer to the analogous component or portion of another strut, though for clarity in the drawings, each component of each strut is not labeled.

Each strut 110 may comprise a distal portion 112, a distal apex 114, a transition portion 116, a proximal apex 118, and a proximal portion 120. Further, in some embodiments, the proximal portion 120 may comprise two separate legs, a first proximal leg 122a and a second proximal leg 122b. In the embodiment of FIG. 1, the first 122a and second 122b proximal legs comprise a distal ends 124a, 124b, diverging portions 126a, 126b, converging portions 127a, 127b, and proximal ends 128a, 128b.

In the embodiment of FIG. 1, the first 122a and second 122b proximal legs are coupled adjacent their distal ends 124a, 124b at a junction 121. The proximal legs 122a, 122b diverge along the diverging portion 126a, 126b of each then extend toward each other along the converging portions 127a, 127b. The proximal legs 122a, 122b of each strut 110 are coupled to the proximal axial portion 105 adjacent the proximal ends 128a, 128b of each of the proximal legs 122a, 122b. Thus, each set of proximal legs 122a, 122b associated with a single strut 110 may form a roughly triangular shape, with the diverging portions 126a, 126b forming the base of the triangle and the converging portions 127a, 127b forming the sides of the triangle. In other embodiments, the diverging portions 126a, 126b may be relatively longer with respect to the converging portions 127a, 127b, thus forming a diamond shape.

FIG. 1A is a detail view taken around line 1A-1A of a proximal apex 118. As shown in this view, and in FIG. 1, in some embodiments, each strut 110 may comprise a barb 130 coupled the strut 110 near the proximal apex 118, the distal apex 114, or both. In the illustrated embodiment, the barb 130 is integrally formed from the material of the strut 110. Further, the barb 130 may be cut from a central portion of the strut 110, meaning the barb 130 is formed by a generally "U-shaped" cut in the strut 110, which cut does not intersect the edges of the strut 110. In other embodiments the barb 130 may be cut from another part of the strut 110 or be comprised of a separate piece of material coupled to the strut 110. In still other embodiments, the barb 130 may be in the form of a spur of strut 110 material; in such embodiments, the barb 130 may be formed by cutting the strut 110 only part way through, as in the barb of a fish hook. As further explained below, barbs 130 may be configured to extend into a body lumen wall, in order to minimize migration of the filter within the lumen.

While in the embodiment of FIG. 1, each strut 110 comprises a barb 130 at the proximal apex 118 and a barb 130 at the distal apex 114, in other embodiments barbs 130 may only be located only at some apexes 118, 114 or only on some struts 110.

In the illustrated embodiment, the barbs 130 are oriented such that the barbs 130 associated with the proximal apexes 118 face the opposite direction from the barbs 130 associated with the distal apexes 114. Specifically, in the illustrated embodiment, the barbs 130 associated with the proximal apexes 118 are oriented such that each barb 130 extends from the strut 110 toward to the distal end 102 of the filter 100. The barbs 130 associated with distal apexes 114 extend toward the proximal 101 end of the filter 100. In some embodiments, filters with bi-directional barbs 130, meaning filters with some barbs oriented in opposite directions than other barbs (as described above) may be configured to prevent migration of the filter 100 in either direction along a body lumen. In other words, each barb 130 may be configured to generally prevent migration of the filter 100 in the direction the barb 130 is oriented; thus, filters with bi-directional barbs 130 may be configured to resist migration in both directions.

FIG. 1B is a detail view of the proximal hook 103. In the illustrated embodiment, the proximal hook 103 is integrally formed with the proximal axial portion 105. Likewise, in the illustrated embodiment, the distal hook 104 is integrally formed with the distal axial portion 106. In other embodiments one or both hooks 103, 104 may be formed from another piece of material and coupled to the filter 100. Further, some embodiments may comprise only a single hook. In some embodiments, one or both hooks 103, 104 may be configured to restrain the axial displacement of the filter 100 during deployment, retrieval, or repositioning of the filter 100.

Like the hooks 103, 104, it is within the scope of this disclosure for the other components (such as the struts 110, barbs 103, and/or the proximal legs 122a, 122b) to be integrally formed with the other components, or be comprised of separate components coupled together.

Figure 2:
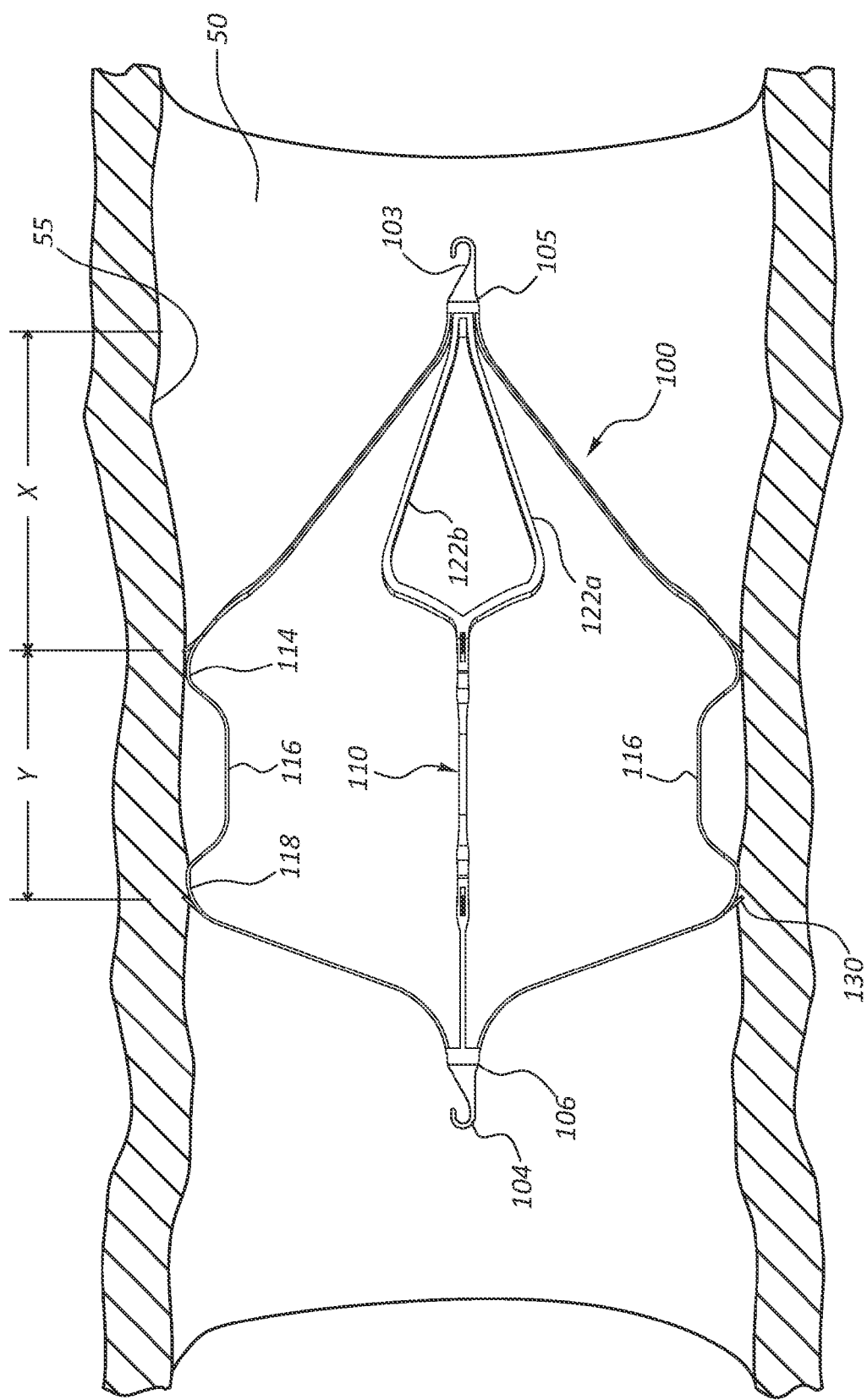
FIG. 2 is a side view of the filter of FIG. 1, disposed within a body lumen.

FIG. 2 is a side view of the filter of FIG. 1, disposed within a cross sectional view of a body lumen 50. As shown in FIG. 2, the filter 100 may be configured such that the proximal apexes 118 and the distal apexes 114 of each strut 110 are sufficiently displaced from the longitudinal axis of the filter 100 that the apexes 118, 114 contact the lumen wall 55 when the filter 100 is disposed within such a lumen 50.

In the embodiment of FIG. 2, each of the proximal apexes 118 is located at substantially the same longitudinal position along the axis of the filter 100 as the other proximal apexes 118. Similarly, each of the distal apexes 114 is located at substantially the same longitudinal position as the other distal apexes 114. In some embodiments the proximal apexes 118 may be displaced a distance along the longitudinal axis of the filter 100 from the distal apexes 114. In the illustrated embodiment, this displacement is labeled as distance "Y." In some embodiments, distance Y may be configured to maintain the position of a filter substantially in the center of a body lumen. For example, in some instances, a relatively greater distance, Y, between the proximal apexes 118 and the distal apexes 114 may increase the stability of the filter 100 within the lumen 50 and minimize the degree to which the filter can rotate out of axial alignment with the lumen 50. In some embodiments distance Y may be from about 0.200 inches to about 1.000 inches.

More particularly, distance Y, may affect the stability of the filter 100 in some instances by preventing the degree to which the filter 100 may rotate or pivot within the lumen 50. Contact between both the proximal apexes 118 and the distal apexes 114 of the filter 100 and the lumen wall 55 may tend to keep the filter 100 centered within the body lumen 50. Relatively larger values of Y may provide relatively stable contact between the filter 100 and the lumen wall 55 and prevent pivoting of the filter 100 as compared to relatively smaller values of Y. Thus, the migration of either the proximal 101 or distal 102 end of the filter 100 toward the body lumen wall 55 may be prevented or minimized. Accordingly, in the event that a medical practitioner wishes to remove or relocate the filter 100, the hooks 103, 104 may remain spaced from the inner wall of the body lumen 50 and be readily accessible to the practitioner. Furthermore, in some applications the tendency of the filter 100 to remain centered within the lumen 50 may maintain the relative positions and orientations of the filtering surface (discussed further below) within the lumen 50.

FIG. 2 also illustrates how, when deployed within a body lumen 50, the barbs 130 of the filter 100 may extend into the body lumen wall 55, further stabilizing the filter 100.

The proximal 118 and distal 114 apexes may comprise the portions of the struts 110 with the largest radial displacement from the longitudinal axis of the filter 100. For instance, in the illustrated embodiment, the transition portions 116 are displaced radially inward from the apexes 118, 114. Likewise, the proximal 120 and distal 112 portions may extend radially from the proximal 105 and distal 106 axial portions to the proximal 118 and distal 114 apexes. Thus, the proximal 118 and distal 114 apexes may be the only portion of the filter 100 configured to contact the lumen wall 55 when the filter 100 is disposed within a body lumen 50. This may reduce irritation or injury caused by contact between the filter 100 and the body lumen 50. Likewise, relatively minimal contact between the filter 100 and the lumen wall 55 may facilitate removal or repositioning of the filter 100 while minimizing trauma to the body lumen 50.

Again, in other embodiments, the proximal apexes 118 may not all be positioned at the same longitudinal position. Similarly, the distal apexes 114 may or may not be disposed at the same longitudinal positions. Nevertheless, a length of longitudinal offset, such as distance Y between some of the apexes 118, 114 may still tend to maintain the axial alignment of the filter 100 in such embodiments.

Referring to both FIG. 1 and FIG. 2, the proximal legs 122a, 122b of the filter 100, taken together, may be configured to define a generally conical or frustoconical shape. This shape may define a filtering surface of the filter 100. In other words, in some embodiments, the cage or matrix formed by the proximal legs 122a, 122b may be configured to trap clots or other materials within the lumen 50. As used herein, "cage" or "matrix" refers to a skeleton structure formed by portions of the struts which may act as a filter. A "cage" is not necessarily an enclosed area, as the skeletal struts comprising a single filtering surface may be referred to as a cage.

Figure 3:
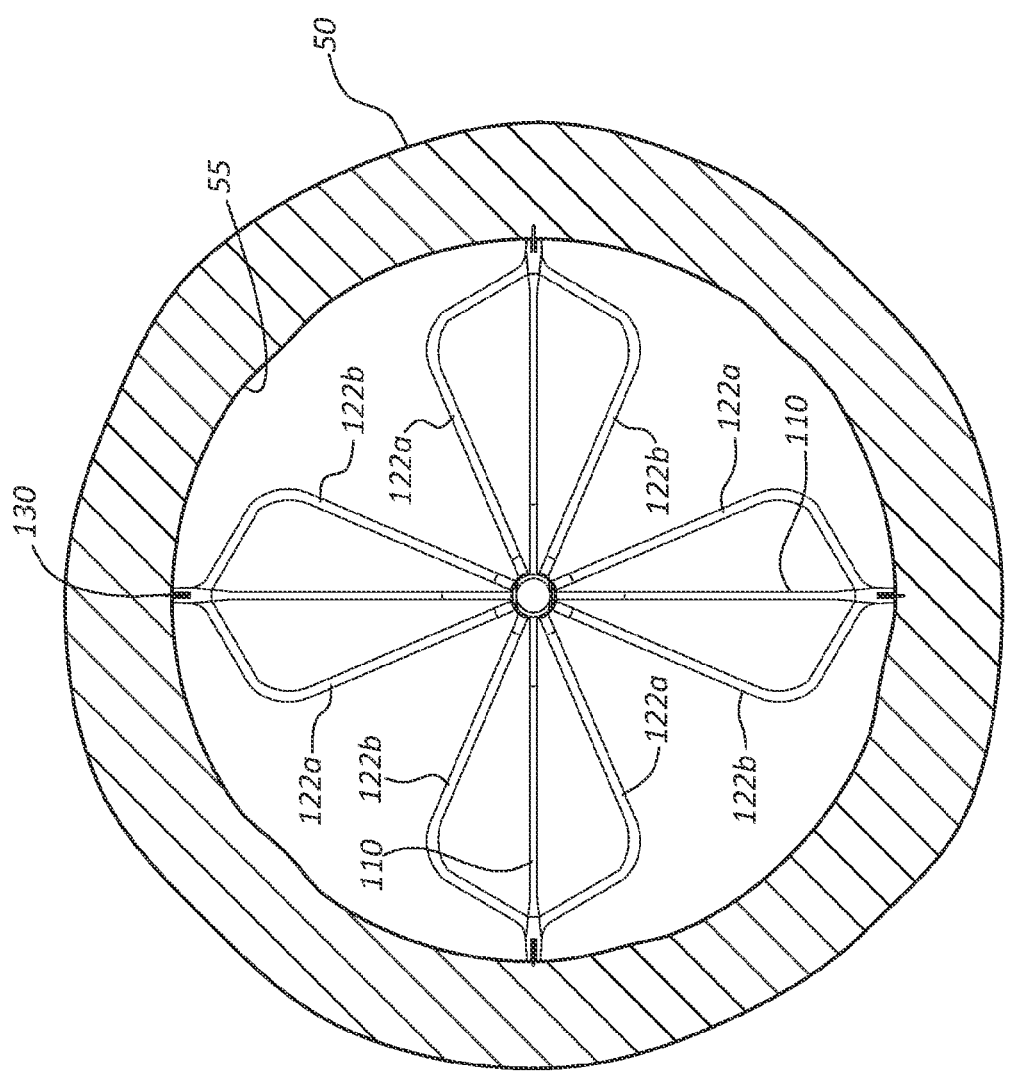
FIG. 3 is an end view of the filter of FIGS. 1 and 2, disposed within the body lumen of FIG. 2.

For example, FIG. 3 is an end view of the filter 100 of FIGS. 1 and 2, disposed within the body lumen 50 of FIG. 2. This end view illustrates the filtering profile formed by the proximal legs 122a, 122b of the struts 110 through which a clot would have to pass to move through the filter 100. FIG. 3 further illustrates the barbs 130 extending into the body lumen wall 55.

Referring again to FIGS. 1 and 2, the conical filtering surface may be configured to "funnel" clots captured by the filter 100 toward the center of the filter 100. In some embodiments, the filter 100 is configured to be disposed such that the flow within the lumen 50 is from the distal end 102 of the filter 100 toward the proximal end 101. Thus, clots caught by the filtering surface may tend to migrate along the proximal legs 122a, 122b toward the point of the cone, located adjacent the proximal axial portion 105 of the filter 100. For example, interaction between the sloped proximal legs 122a, 122b of the conical filter and the force of the flow acting on clots may tend to push the clots toward the center of the cone. Directing clots toward the center of the filter 100 may provide an enhanced flow profile through the filter 100 even when the filter 100 is partially full of clots. Further, concentrating the clots within the center of the blood flow may promote breakup of the clots and/or reduce the occurrence of thrombosis from clots in contact with the lumen wall 55. In some embodiments, the filter 100 is configured to catch clots in the matrix of proximal legs 122a, 122b, but generally allow clots to pass the sparser matrix formed by the distal portions 120 of the struts 110.

FIG. 2 further illustrates a distance "X" corresponding to the length of the cone portion of the filter 100. The filter 100 may be configured such that the value of X is relatively large, in other words that the length of the cone portion of the filter 100 is relatively large as compared to other parameters of the filter 100. In some embodiments, the length of X may be designed to maximum X while creating a filter 100 of a particular overall length with a Y value large enough to provide desired stability to the design. In some embodiments the length of X will be altered by the size of the lumen 50 within which the filter 100 is disposed. In lumens of small diameters (which tend to compress the entire filter radially) the radial compression of the proximal apexes 118 may reduce the size of the base of the cone and thus extend the length, X, of the cone. Furthermore, the length of the cone may tend to elongate when the filter 100 is drawn into a sheath. In some embodiments, X may range from about 0.300 inches to about 2.000 inches when the filter is unconstrained.

Figure 4:
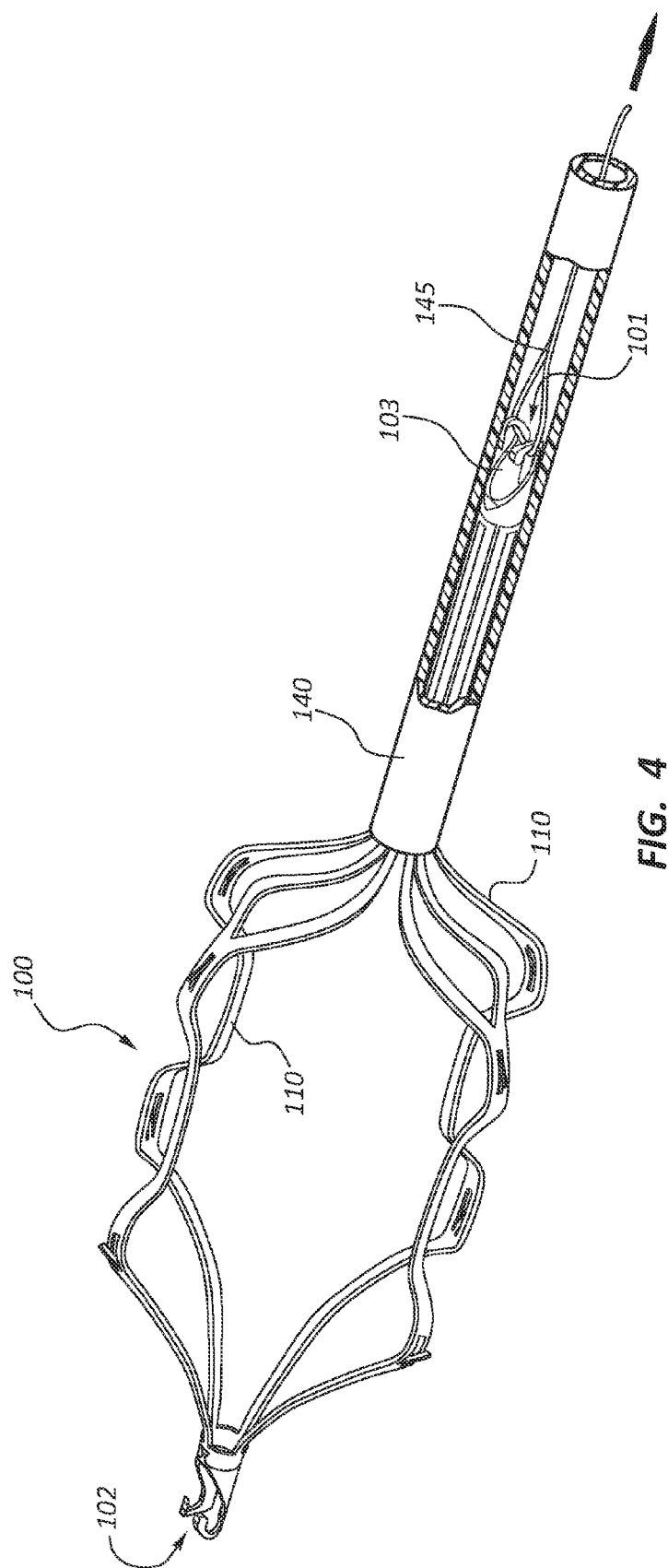
FIG. 4 is a perspective view of the filter of FIG. 1, partially disposed within a catheter.

FIG. 4 is a perspective view of the filter 100 of FIG. 1, partially disposed within a sheath, such as catheter 140. In the illustrated embodiment, the proximal hook 103 of the filter 100 is restrained by a snare 145. Displacing the snare 145 proximally with respect to the catheter 140 will tend to draw the filter 100 into the catheter 140.

In some embodiments, drawing the filter 100 into a catheter 140 may tend to radially retract the struts 110 as the filter 100 is drawn in. In other words the apexes 118, 114 may begin to disengage the lumen wall when only a small portion of the filter 100 is drawn into the catheter 140. Further, radial contraction of the struts 110 may tend to straighten the curvature of the struts 110 and thereby cause the barbs 130 to become more aligned with surrounding portions of the struts 110.

In the embodiment of FIG. 4, the filter 100 is being drawn into the catheter 140 by the proximal hook 103 of the filter 100. Filters which may be drawn into a catheter 140 from either the proximal 101 or distal 102 ends are likewise within the scope of this disclosure.

The filter 100 may be drawn into the catheter 140 in order to use the catheter 140 to place the filter 100 within a body lumen of a patient. Furthermore, the filter 100 may be partially or fully drawn back into the catheter 140 after the filter 100 is placed within the body lumen, in order to move the filter 100 within the body lumen, or to completely remove the filter 100 from the body lumen. The filter 100 may therefore be configured to be removed or permanently disposed within a body lumen of a patient.

In some embodiments, the filter 100 may be comprised of a shape memory alloy, for example Nitinol. Thus, the filter 100 may be comprised of a material which, is first "set" in a particular shape when the filter 100 is being manufactured, then tends to return to that shape if it is subsequently deformed. The filter 100 may be "set" in the expanded configuration, or the shape generally shown in FIGS. 1-3. Drawing the filter 100 into a catheter 140, as shown in FIG. 4, may thus temporarily compress the legs struts 110 within the catheter 140, though the filter 100 may be configured to return to the expanded shape upon deployment from the catheter 140. Thus, a filter may be configured with radially expanding struts which are elastically compressible into a position substantially parallel with the axis of the filter.

In some embodiments the filter 100 may be configured such that, when the filter 100 is deployed from a catheter 140, either the proximal 118 or distal 114 apexes engage the lumen walls before the other set of apexes.

Figure 5:
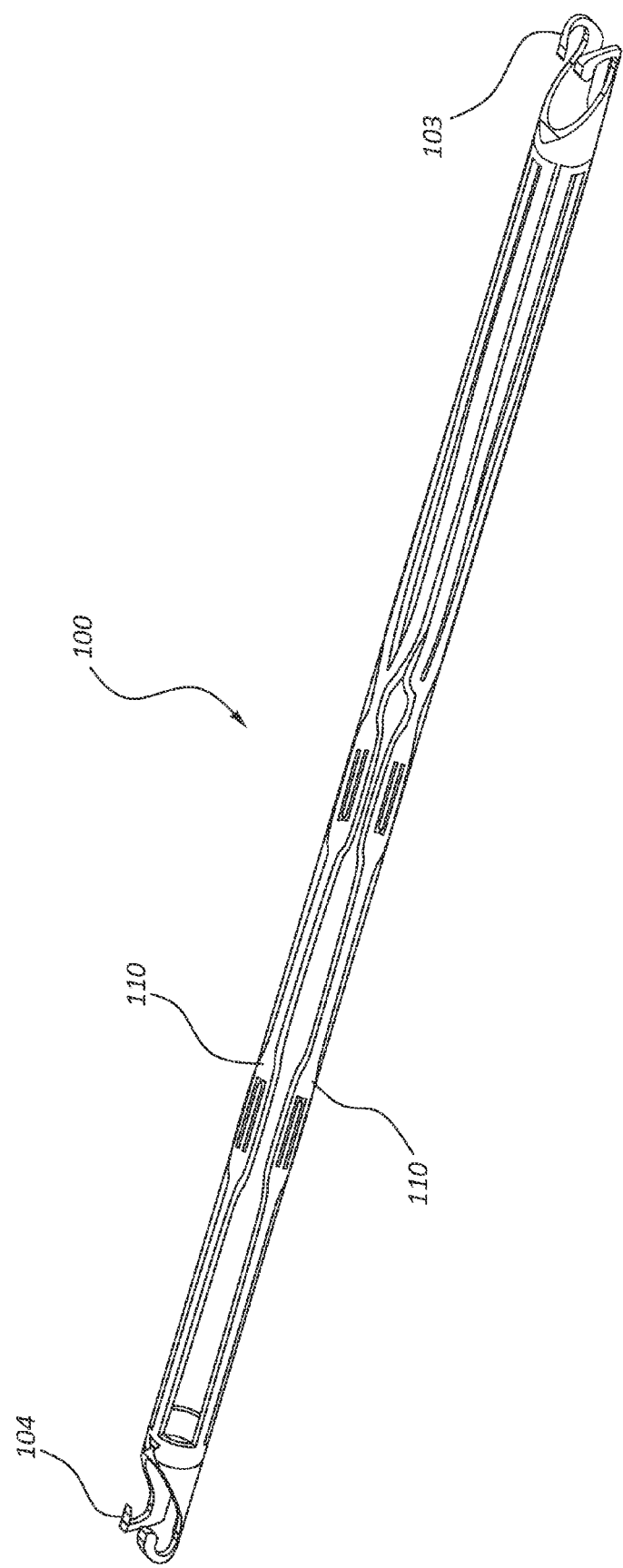
FIG. 5 is a perspective view of the filter of FIG. 1, in a pre-expanded state.

FIG. 5 is a perspective view of the filter 100 of FIG. 1, in a pre-expanded state. FIG. 5 illustrates how, in some embodiments, the filter 100 may be formed from a single, integral tube of material. The components of the filter 100 may be formed by cutting or other methods. The shape of each component may first be cut, for example, by laser cutting, and any excess material subsequently removed. The components may then be formed, and set, into the desired shape of the filter 100. FIG. 5 illustrates a filter 100, formed from a single tube of material after the tube has been cut and the excess material removed, but before shaping. Thus, the struts 110 (and all portions thereof) all lie on the same cylinder—the tube from which they were formed—prior to shaping. FIG. 5 also illustrates the proximal 103 and distal 104 hooks of the filter 100. Alternatively, the filter 100 could be formed from a flat piece of material that is cut, expanded and then welded together to form the filter 100. Additionally, the filter 100 could be created by cutting wire into the shape of the filter and then welding it into the desired geometry.

The filter 100 may then be expanded to its deployed shape. In some embodiments the filter 100 may be comprised of a material that, once formed into a particular shape, will tend to return to that shape. Again, it is within the scope of this disclosure to create the filter from super elastic materials, such as Nitinol.

Figure 6A:
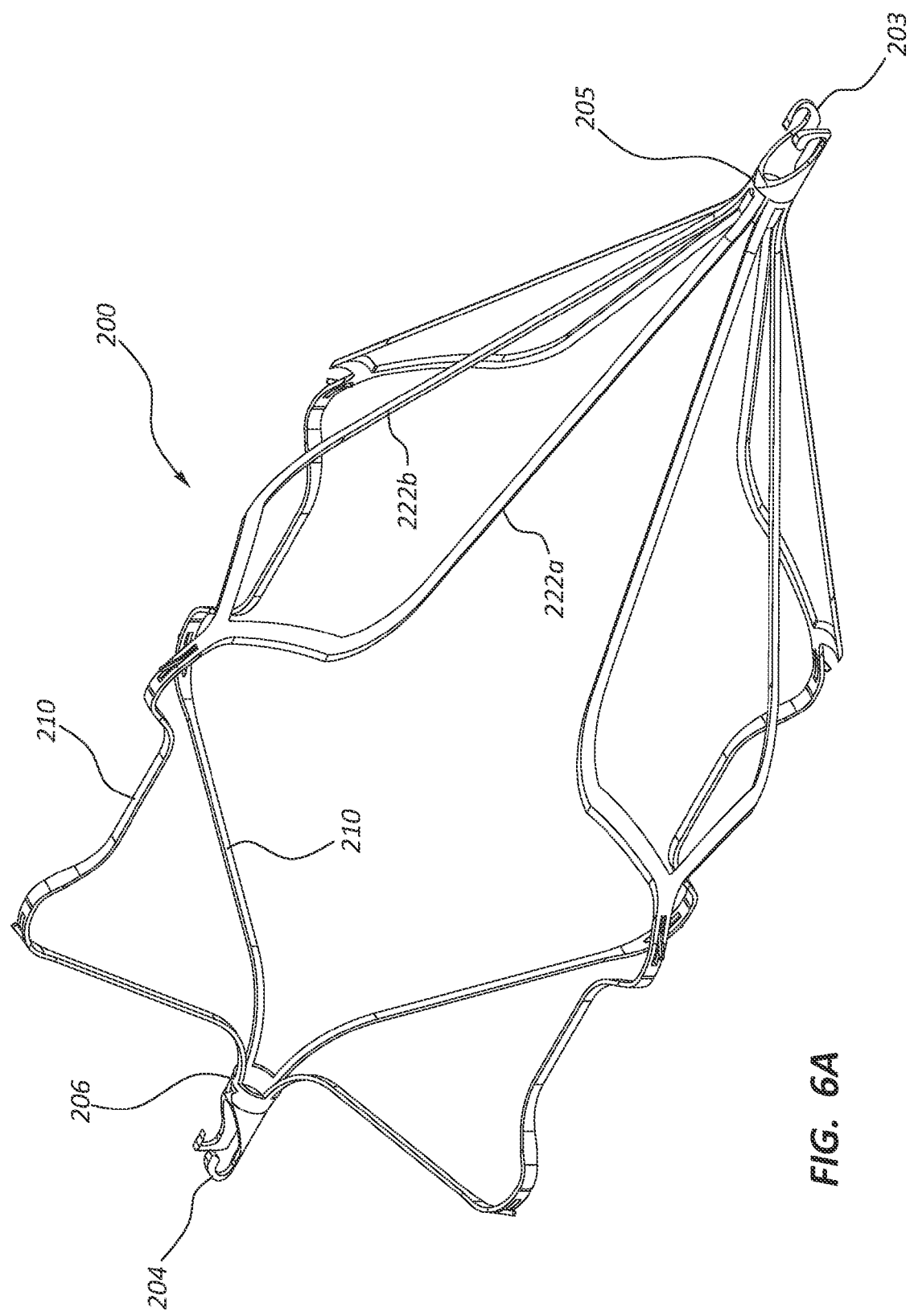
FIG. 6A is a perspective view of another embodiment of a filter.
Figure 6B:
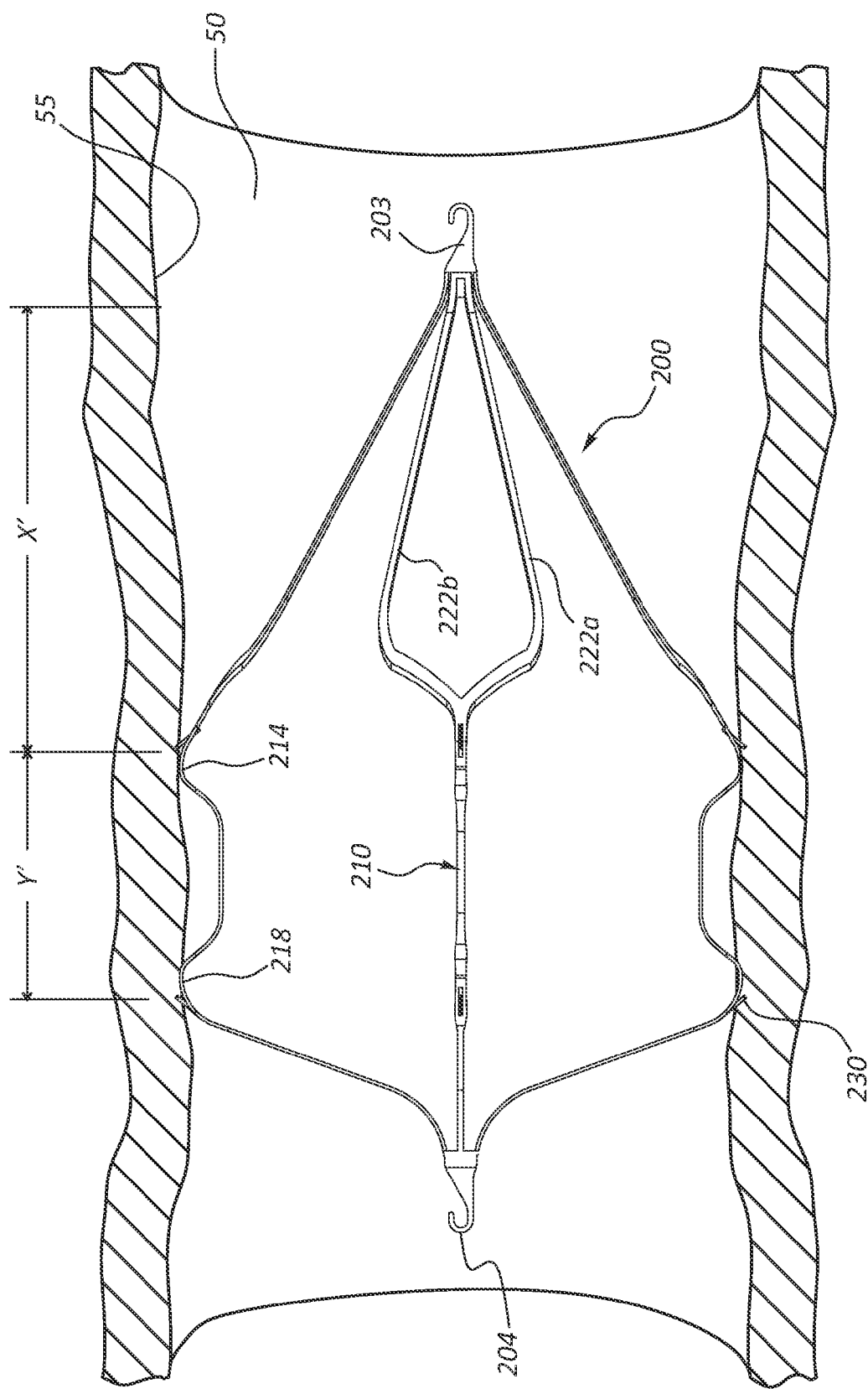
FIG. 6B is a side view of the filter of FIG. 6A.

FIGS. 6A and 6B are views of another embodiment of a filter that can, in certain respects, resemble components of the filter described in connection with FIGS. 1-5. It will be appreciated that all the illustrated embodiments may have analogous features. Accordingly, like features are designated with like reference numerals, with the leading digits incremented to "2." (For instance, the filter is designated "100" in FIG. 1 and an analogous filter is designated as "200" in FIG. 6A.) Relevant disclosure set forth above regarding similarly identified features thus may not be repeated hereafter. Moreover, specific features of the filter and related components shown in FIGS. 6A and 6B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the filter of FIGS. 6A and 6B. Any suitable combination of the features, and variations of the same, described with respect to the filter and components illustrated in FIGS. 1-5, can be employed with the filter and components of FIGS. 6A and 6B, and vice versa. This pattern of disclosure applies equally to further embodiments depicted in subsequent figures and described hereafter.

FIG. 6A is a perspective view, and FIG. 6B is side view, of another embodiment of a filter 200. The filter 200 comprises proximal 203 and distal 204 hooks as well as proximal 205 and distal 206 axial portions. A plurality of struts 210 extend between, and are coupled to, the proximal 205 and distal 206 axial portions. As in the embodiment of FIG. 1, the filter 200 comprises proximal legs 222a, 222b which may collectively form a conical filtering surface or cage.

As shown in these figures, and as referenced above, in some embodiments a filter 200 may be configured with a conical filter section that is relatively longer or shorter than in other embodiments. For instance, the conical section, distance X', is relatively larger with respect to Y' than the conical section, distance X (with respect to Y) of FIGS. 1 and 2. Larger conical segments may provide particular filtering capabilities. In some embodiments, Y' may be from about 0.200 inches to about 1.000 inch while X' may range from about 0.300 inches to about 2.000 inches in some embodiments.

Figure 7A:
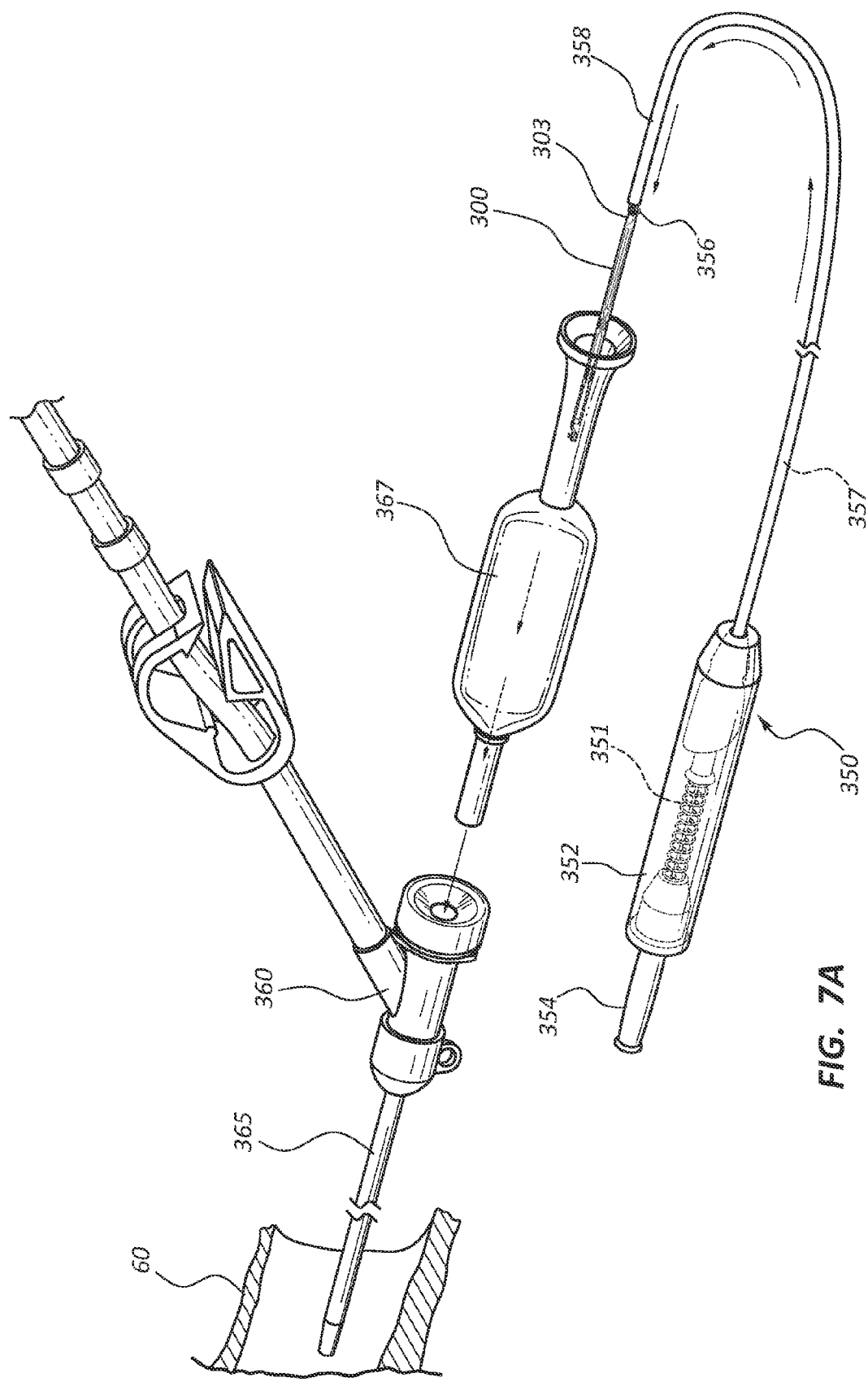
FIG. 7A is a perspective view of a delivery system in a first configuration.

FIG. 7A is a perspective view of a delivery system in a first configuration. The illustrated delivery system comprises a deployment device 350, a hub 360, a delivery catheter 365, and an introducer 367. In some aspects the delivery system may comprise analogous components to the snare and catheter discussed in connection with FIG. 4. It will be appreciated by one skilled in the art having the benefit of this disclosure that the delivery system described herein may be used in connection with other filters or devices in addition to the filter disclosed herein.

In the embodiment of FIG. 7A, the deployment device 350 comprises a handle 352, a button 354, a loop 356, and a loop sheath 358. The loop 356 may extend from a distal end of the loop sheath 358. Further the loop 356 may be coupled to an inner member 357 disposed within a lumen of the loop sheath 358. Displacement of the inner member 357 distally with respect to the loop sheath 358 may be configured to cause the loop 356 to extend further from the distal end of the loop sheath 358. The inner member 357 may be coupled to the button 354 such that depressing the button 354 causes the inner member 357 to be displaced distally with respect to the loop sheath 358.

In the illustrated embodiment, the loop 356 is secured around a proximal hook 303 of a filter 300. The filter 300 is illustrated in a radially constrained configuration. In some embodiments the filter 300 may be radially constrained by the introducer 367, including embodiments where the filter 300 is disposed within the introducer 367. The introducer 367 may extend into the hub 360, such that the introducer 367 and hub 360 are in communication with an inner lumen of the delivery catheter 365.

The deployment device 350 may be configured to displace the filter 300 both proximally and distally; for example, within the introducer 367, the hub 360, the delivery catheter 365 or other components. Specifically, the deployment device 350 may be configured such that distally displacing the deployment device 350 with respect to a surrounding component, such as the introducer 367 distally displaces the filter 300 with respect to the surrounding component due to interaction of the loop sheath 358 and the filter 300. In other words, the loop sheath 358 may be configured to transfer a distally directed force to the filter 300.

The loop 356 may be configured to allow proximal displacement of the filter 300 with respect to a surrounding component. In the illustrated embodiment, the loop 356 extends only a small distance from the loop sheath 358 and is engaged with the proximal hook 303 of the filter 300. Pulling the deployment device 350 proximally may thus transfer proximal force to the filter 300 through the interaction of the proximal hook 303 and the loop 356. Thus the deployment device 350 may be configured to allow a practitioner to both advance and retract the filter 300 with respect to surrounding components such as the introducer 367, the hub 360, or the delivery catheter 356.

The handle 352 of the deployment device 350 may comprise a biasing member 351 configured to provide a distally directed force on the inner member 357. Thus, the biasing member 351 may be configured to provide secure engagement of the loop 356 to the filter 300 (via the proximal hook 303 in the illustrated embodiment). As further discussed below, depressing the button 354 may overcome the force of the biasing member 351 causing the loop 356 to extend from the loop sheath 358 to release the proximal hook 303.

Figure 7B:
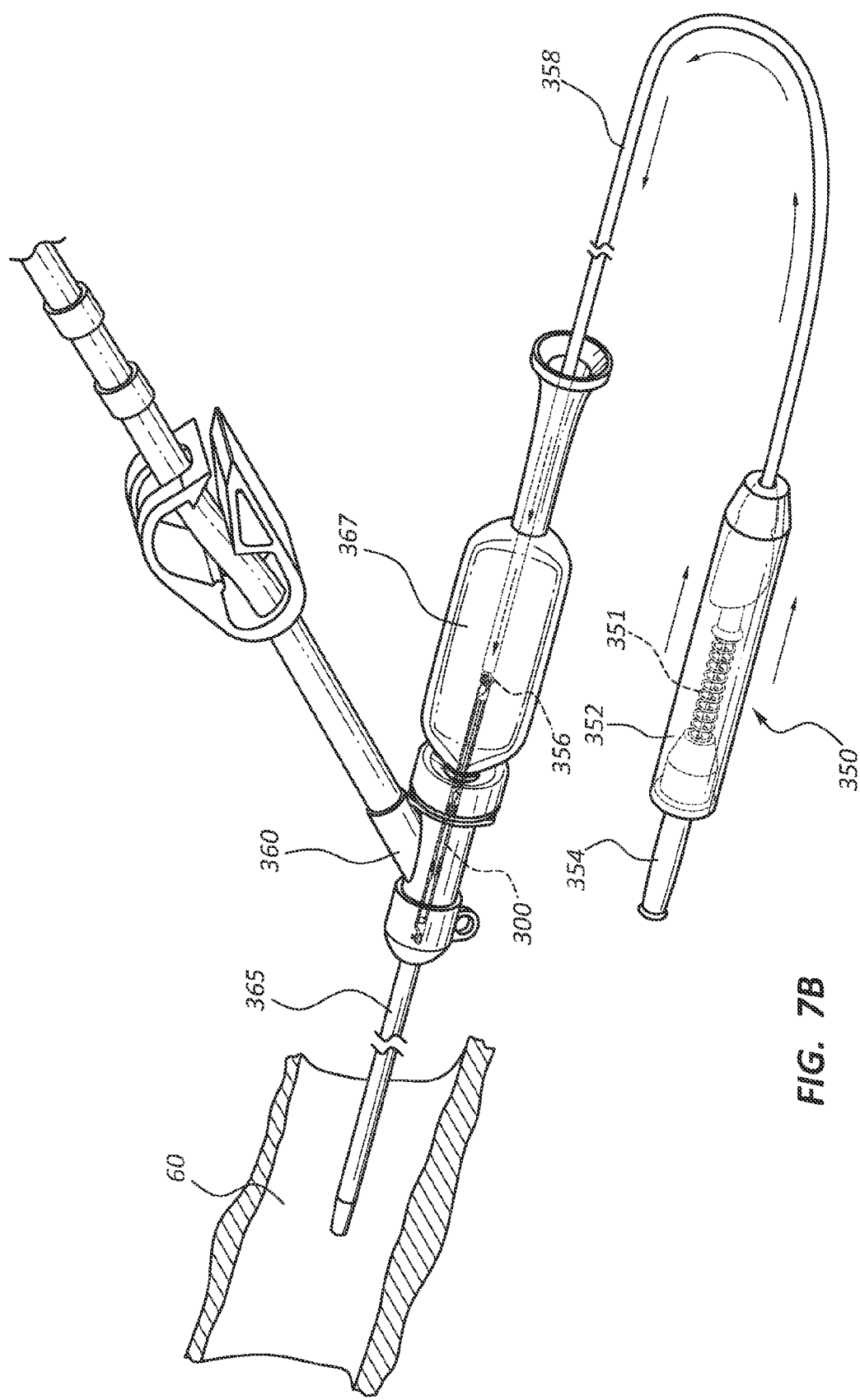
FIG. 7B is a perspective view of the delivery system of FIG. 7A in a second configuration.
Figure 7C:
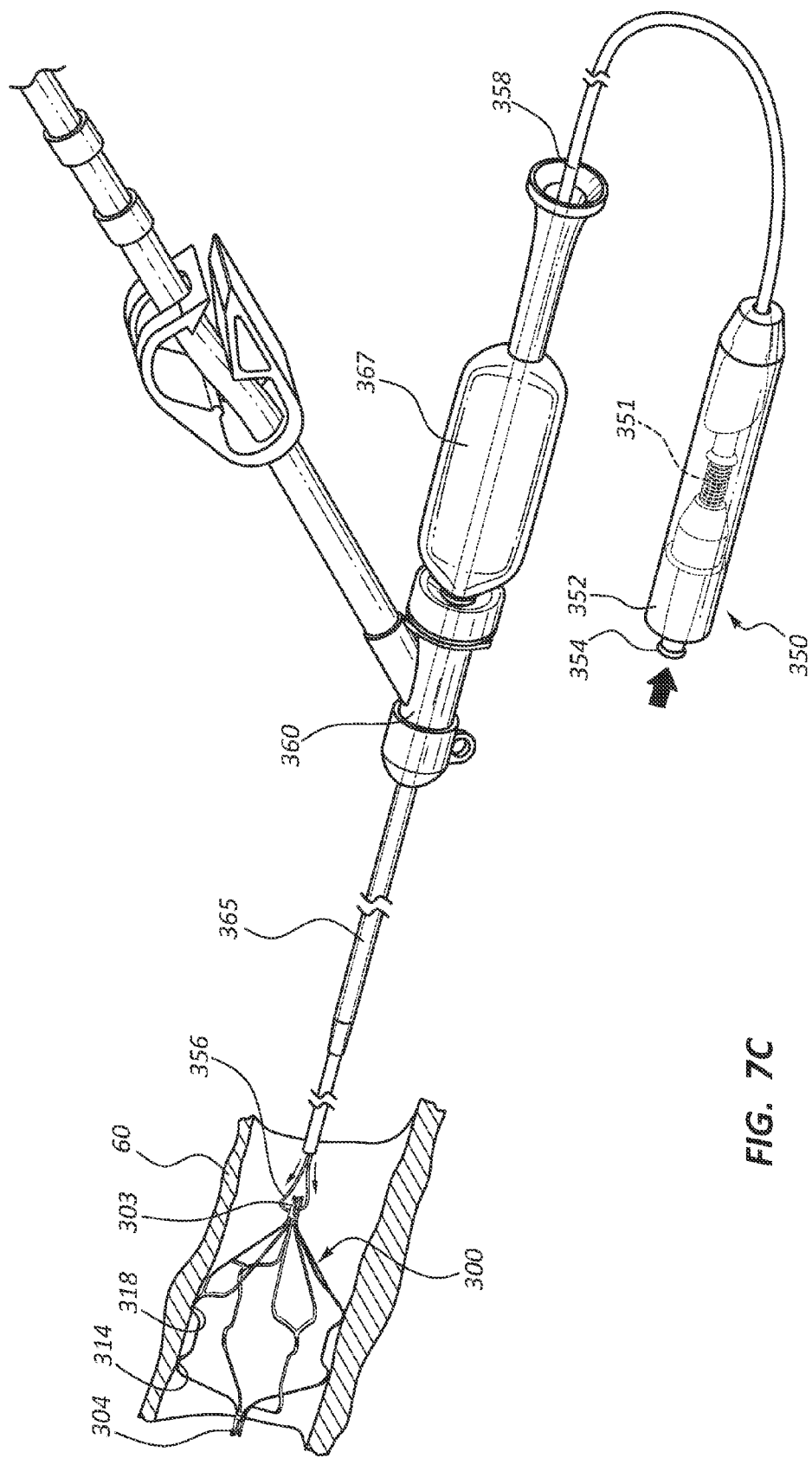
FIG. 7C is a perspective view of the delivery system of FIGS. 7A and 7B in a third configuration.

FIGS. 7A-7C illustrate an exemplary filter delivery procedure. In the exemplary procedure, the filter 300 may be translated from the introducer 367, through the hub 360, and down the delivery catheter 365 by distally displacing the deployment device 350 as indicated by the arrows in FIGS. 7A and 7B. The filter 300 may be prepackaged in the introducer 367 prior to the therapy or disposed within the introducer 367 through other means. In other embodiments, the system may be configured with no introducer 367 and/or no hub 360, with the filter 300 directly disposed within the delivery catheter 365. This includes embodiments wherein the filter 300 is packaged within the delivery catheter 365 by a manufacturer.

At any point during delivery of the filter 300 a practitioner may advance or retract the filter 300 as described above. In particular, in some embodiments a filter, such as filter 300, may slip or "jump" as the struts 310 of the filter 300 begin to expand as the filter 300 is deployed form the delivery catheter 365. For example, the radial expansion of the struts 310 (as the filter 300 is deployed) may exert a proximally oriented force on the distal end of the delivery catheter 365 as the angled portions of the struts 310 interact with the delivery catheter 365. As the filter 300 is deployed, friction between the filter 300 and the delivery catheter 365 lumen may be reduced as the proportion of the filter 300 within the delivery catheter 365 is decreased. Further, distal displacement of the filter 300 with respect to the catheter may change the coefficient of friction from a static coefficient to a dynamic coefficient. Thus, it may be difficult for a practitioner to determine exactly when a filter 300 may tend to jump during the deployment process. Erratic movement of the filter 300 may complicate placement of the filter 300 or cause injury to the body lumen 60.

Thus, the loop 356 may be configured to restrain the proximal displacement of the filter 300 and prevent or minimize the tendency of the filter 300 to jump during deployment. Further, the loop 356 and the loop sheath 358 may enable a practitioner to partially retract and/or partially deploy the filter 300, and readjust the position of the filter 300 proximally or distally as necessary. Additionally, in some embodiments a practitioner may slowly deploy the filter such that one set of apexes (such as the distal apexes 314) engage the lumen wall before the filter 300 is fully deployed. Contact between the deployed apexes and the lumen may also tend to mitigate jumping and stabilize the filter.

Once the filter 300 is fully deployed with the body lumen 60, as illustrated in FIG. 7C, a practitioner may depress the button 354 of the handle 352 to extend the loop 358 and allow for disengagement of the loop 358 and the proximal hook 303 of the filter 300. It should be noted that though the filter 300 is described as being deployed with the proximal hook 303 engaged with the loop 358, in other embodiments the filter 300 may be oriented in the opposite direction within the delivery catheter 365 and the distal hook 304 positioned adjacent to, and engaged with, the loop 358.

FIG. 8A is a side view of the handle 352 of the deployment device 350 of FIGS. 7A-7C, in a first configuration while FIG. 8B is a side view of the handle 352 of the deployment device 350 in a second configuration. The handle 352 may include a button 354 and an inner member 357 as described above. A biasing member 351 may be configured to apply a proximally oriented force to the button 354 and the inner member 357. The biasing member 351 may comprise a spring in some instances.

As indicated by the arrow in FIG. 8B, depressing the button 354 may overcome the biasing member 351 and cause the inner member 357 to be displaced in a distal direction.

Exemplary Filter Embodiments

According to one exemplary embodiment, a filter for a body lumen is disclosed, which comprises a first axial portion adjacent a first end of the filter; a second axial portion adjacent a second end of the filter; and a plurality of struts disposed between and coupled to the first and second axial portions. Each strut comprises a first apex; a second apex offset a longitudinal distance from the first apex; and a first leg and a second leg, each disposed between the first apex and the first axial portion.

The first and second legs of the filter may extend radially outward from the first axial portion when the legs are expanded.

The filter may further comprise a plurality of barbs coupled to the struts.

The plurality of barbs of the filter may be coupled to the struts adjacent each of the first and second apexes.

Furthermore, in some embodiments the barbs of the filter associated with first apexes are oriented in a different direction than the barbs associated with the second apexes.

Additionally, the plurality of barbs may be integrally formed with the struts.

Moreover, the plurality of barbs may be formed from center portions of the struts.

In some embodiments, each barb is configured to align with a portion of the strut to which the barb is coupled, when the struts are drawn into a catheter.

The first axial portion and the second axial portion of the filter may comprise a tube, and in some configurations the filter is integrally formed from the material of the tube, and may be cut from a tube of shape memory alloy.

The first legs and the second legs of the filter form a substantially conical or frustoconical cage in some embodiments.

The filter may be configured to direct clots to a center of the conical or frustoconical cage.

Additionally, the first end of the filter may be configured to be nearest the heart when the filter is deployed.

Additionally, a filter for a body lumen is disclosed which comprises a first axial portion adjacent a first end of the filter; a second axial portion adjacent a second end of the filter; and a plurality of struts disposed between and coupled to the first and second axial portions. Each strut may comprise a first apex; and a second apex offset a longitudinal distance from the first apex; such that each first apex and each second apex is configured to contact a vessel wall when the filter is deployed.

In some embodiments, each strut further comprises a transition portion disposed between the first apex and the second apex, the transition portion disposed substantially parallel to a longitudinal axis of the filter when the filter is deployed, and wherein the transition portion is disposed radially inward from the first and second apexes.

Additionally or alternatively, each strut further comprises a first leg; and a second leg wherein the first leg and the second leg are each disposed between the first apex and the first axial portion.

In some configurations the first legs and the second legs form a substantially frustoconical cage.

The filter may be configured to direct clots to a center of the frustoconical cage.

Additionally, the first end of the filter may be configured to be nearest the heart when the filter is deployed.

Exemplary Methods

A method of deploying a filter is disclosed which comprises inserting a filter into a body lumen. The filter comprises plurality of struts, each strut of the plurality of struts extending between a first axial portion adjacent a first end of the filter and a second axial portion adjacent a second end of the filter, each strut comprising a first apex and a second apex offset a longitudinal distance from the first apex, and wherein a portion of the plurality of struts comprises a conical filtering portion. The method also comprises deploying the first axial portion and the first apexes of the plurality of struts such that the first apexes contact a body lumen, deploying the second apexes, stabilizing the filter by contact between the first apexes and the body lumen while deploying the second apexes, and contacting the body lumen with the second apexes, wherein the filter is disposed such that fluid within the body lumen generally flows in a direction from a base of the conical filtering portion to a vertex of the conical filtering portion.

The step of stabilizing the filter may comprise minimizing shift of the filter while the second apexes deploys.

Furthermore, contact between the first apexes and the body lumen may resist jumping of the filter as the second apexes are deployed.

Additionally, each strut of the plurality of struts may further comprise a first leg and a second leg disposed between the first apex and the first axial portion, such that the first and second legs form the conical filtering portion, and wherein deploying the first axial portion and the first apexes further comprises deploying the conical filtering portion.

In another embodiment, a method of deploying a filter comprises inserting a filter into a body lumen, the filter initially disposed in a radially constrained configuration; deploying a conical filtering portion of the filter, the conical filtering portion comprising a plurality of pairs of first and second legs each pair of legs coupled adjacent a first and second end of each leg; deploying a first plurality of apexes, each apex of the first plurality of apexes disposed adjacent one pair of legs; and deploying a second plurality of apexes, each apex of the second plurality of apexes disposed at an end of a transition portion extending between one apex of the first plurality of apexes and one apex of the second plurality of apexes.

Contact between the first plurality of apexes and a body lumen may stabilize the filter while the second plurality of apexes is deployed.

Additionally, contact between the second plurality of apexes and a body lumen may stabilize the filter while the first plurality of apexes is deployed.

A method of filtering clots or other matter in a body lumen is disclosed, which comprises obtaining a filter as described herein and disposing the filter within a body lumen of a patient. In some embodiments, the filter is removably disposed within the body lumen. The body lumen may be the vasculature, such as the inferior vena cava.

A method of deploying a filter is disclosed, which comprises obtaining a filter as described herein, obtaining a filter deployment device as described herein, and displacing the filter proximally and distally within a body lumen by displacing the filter deployment device. The method of deploying a filter may further comprise displacing the actuator with respect to the handle to decouple the filter from the filter deployment device. The method may further comprise controlling jumping of the filter during deployment by controlling the position of the inner member.

Exemplary Filter Deployment Devices and Related Kits

A filter deployment device is disclosed which is configured to displace a filter within a body lumen, the filter deployment device comprising: an elongate sheath; an inner member axially displaceable within the elongate sheath; a filter coupling component coupled to a distal end of the inner member; a handle coupled to a proximal end of the elongate sheath; and an actuator operatively coupled to the handle and the inner member such that displacement of the actuator with respect to the handle displaces the inner member with respect to the elongate sheath.

The filter deployment device may further comprise a biasing member disposed within the handle, the biasing member configured to exert a proximal biasing force on the inner member with respect to the elongate sheath.

The filter coupling component of the filter deployment device may comprise a loop.

In some embodiments, the combination of contact with a distal end of the elongate sheath and contact with the filter coupling component is configured to both proximally and distally displace a filter.

Displacement of the actuator with respect to the handle of the filter deployment device may be configured to decouple a filter from the filter deployment device.

In some embodiments, the biasing member tends to maintain a position of the loop at least partially within the elongate sheath.

Furthermore, displacement of the actuator with respect to the handle may extend the loop distally from a distal end of the elongate sheath.

Additionally, the filter coupling component may be configured to allow a practitioner to restrain jumping of the filter during deployment.

The present disclosure also provides a kit comprising: a filter as described herein and a filter deployment device as also described herein.

The examples and embodiments disclosed herein are to be construed as merely illustrative and exemplary, and not a limitation of the scope of the present disclosure in any way. It will be apparent to those having skill in the art with the aid of the present disclosure that changes may be made to the details of the above-described embodiments without departing from the underlying principles of the disclosure herein. It is intended that the scope of the invention be defined by the claims appended hereto and their equivalents.

The invention claimed is:

1. A filter for a body lumen, comprising:
a first axial portion adjacent a first end of the filter;

a second axial portion adjacent a second end of the filter;
a plurality of struts disposed between and coupled to the first and second axial portions, each strut comprising:
  a first apex;
  a second apex offset a longitudinal distance from the first apex;
  a first portion extending between the first axial portion and the first apex, the first portion of the strut comprising:
    a first leg; and
    a second leg, wherein the first leg and the second leg each extend from a branch point to the first axial portion; and
  a transition portion disposed between the first apex and the second apex, the transition portion disposed radially inward from the first and second apexes.

2. The filter of claim 1, wherein the first and second legs extend radially outward from the first axial portion when the legs are expanded.

3. The filter of claim 1, further comprising a plurality of barbs coupled to the struts.

4. The filter of claim 3, wherein the plurality of barbs are coupled to the struts adjacent each of the first and second apexes.

5. The filter of claim 3, wherein the barbs associated with first apexes are oriented in a different direction than the barbs associated with the second apexes.

6. The filter of claim 3, wherein the plurality of barbs are integrally formed with the struts.

7. The filter of claim 6, wherein the plurality of barbs are formed from center portions of the struts.

8. The filter of claim 3, wherein each barb is configured to align with a portion of the strut to which the barb is coupled, when the struts are drawn into a catheter.

9. The filter of claim 1, wherein the first axial portion and the second axial portion comprise a tube.

10. The filter of claim 9, wherein the filter is integrally formed from the material of the tube.

11. The filter of claim 1, wherein the filter is cut from a tube of shape memory alloy.

12. The filter of claim 1, wherein the first legs and the second legs form a substantially conical or frustoconical cage.

13. The filter of claim 12, wherein the filter is configured to direct clots to a center of the conical or frustoconical cage.

14. The filter of claim 1, wherein the first end is configured to be nearest the heart when the filter is deployed.

15. The filter of claim 1, wherein each strut of the plurality of struts further comprises a second portion that extends between the second axial portion and the second apex, wherein the second portion is unbranched.

16. The filter of claim 15, wherein the first portions of the plurality of struts form a first matrix and the second portions of the plurality of struts form a second matrix, wherein the second matrix is sparser than the first matrix.

17. The filter of claim 1, wherein the first apex is positioned a first distance from a longitudinal axis of the filter and a second apex is positioned a second distance from the longitudinal axis of the filter, wherein the first distance and second distance are of substantially equal length.

18. A method of deploying a filter, comprising:
  inserting the filter of claim 1 into a body lumen, wherein the plurality of struts of the filter form a conical filtering portion;
  deploying the first axial portion and the first apexes of the plurality of struts such that the first apexes contact a body lumen;
  deploying the second apexes;
  stabilizing the filter by contact between the first apexes and the body lumen while deploying the second apexes; and
  contacting the body lumen with the second apexes;
  wherein the filter is disposed such that fluid within the body lumen generally flows in a direction from a base of the conical filtering portion to a vertex of the conical filtering portion.

19. The method of claim 18, wherein stabilizing the filter comprises minimizing shift of the filter while the second apexes deploys.

20. The method of claim 18, wherein contact between the first apexes and the body lumen resists jumping of the filter as the second apexes are deployed.

21. The method of claim 18, wherein the first and second legs of the plurality of struts form the conical filtering portion, and wherein deploying the first axial portion and the first apexes further comprises deploying the conical filtering portion.

22. A method of filtering clots or other matter in a body lumen, comprising:
  obtaining the filter recited in claim 1, and
  disposing the filter within a body lumen of a patient.

23. The method of claim 22, wherein the filter is removably disposed within the body lumen.

24. The method of claim 22, wherein the body lumen is the vasculature.

25. The method of claim 24, wherein the body lumen is the inferior vena cava.

26. A filter for a body lumen, comprising:
  a first axial portion adjacent a first end of the filter;
  a second axial portion adjacent a second end of the filter;
  a plurality of struts disposed between and coupled to the first and second axial portions, each strut comprising:
    a first apex;
    a second apex offset a longitudinal distance from the first apex;
    a first portion extending between the first axial portion and the first apex, the first portion of the strut comprising:
      a first leg; and
      a second leg, wherein the first leg and the second leg each extend from a branch point to the first axial portion; and
    a transition portion disposed between the first apex and the second apex, the transition portion disposed radially inward from the first and second apexes;
    each first apex and each second apex configured to contact a vessel wall when the filter is deployed; and
    wherein each strut extends radially outward from the first axial portion to the first apex of the strut and each strut extends radially outward from the second axial portion to the second apex of the strut.

27. The filter of claim 26, wherein the transition portion of each strut is disposed substantially parallel to a longitudinal axis of the filter when the filter is deployed.

28. The filter of claim 26, wherein the first legs and the second legs form a substantially frustoconical cage.

29. The filter of claim 28, wherein the filter is configured to direct clots to a center of the frustoconical cage.

30. The filter of claim 26, wherein the first end is configured to be nearest the heart when the filter is deployed.

31. A method of deploying a filter, comprising:
  inserting the filter of claim 26 into a body lumen, the filter initially disposed in a radially constrained configuration;

deploying a conical filtering portion of the filter, wherein the conical filtering portion is formed from the first legs and the second legs;
deploying the first apexes; and
deploying the second apexes.

32. The method of claim 31, wherein contact between the first apexes and a body lumen stabilizes the filter while the second apexes are deployed.

33. The method of claim 31, wherein contact between the second apexes and a body lumen stabilizes the filter while the first apexes are deployed.

* * * * *